(12) United States Patent
Kuracina et al.

(10) Patent No.: US 9,987,423 B2
(45) Date of Patent: *Jun. 5, 2018

(54) NEEDLE GUARD

(71) Applicant: Injectimed, Inc., Minden, NV (US)

(72) Inventors: Thomas C. Kuracina, Carson City, NV (US); Tim L. Kitchen, Bethesda, MD (US)

(73) Assignee: Injectimed, Inc., Minden, NV (US)

( * ) Notice: Subject to any disclaimer, the term of this patent is extended or adjusted under 35 U.S.C. 154(b) by 168 days.

This patent is subject to a terminal disclaimer.

(21) Appl. No.: 15/159,403

(22) Filed: May 19, 2016

(65) Prior Publication Data

US 2016/0263353 A1    Sep. 15, 2016

Related U.S. Application Data

(63) Continuation of application No. 15/010,705, filed on Jan. 29, 2016, now Pat. No. 9,415,192, which is a continuation of application No. 14/247,986, filed on Apr. 8, 2014, now Pat. No. 9,440,052, which is a continuation of application No. 13/037,164, filed on Feb. 28, 2011, now Pat. No. 8,764,711.

(51) Int. Cl.
*A61M 5/162* (2006.01)
*A61M 25/06* (2006.01)
*A61M 5/32* (2006.01)
*A61M 25/00* (2006.01)

(52) U.S. Cl.
CPC ........ *A61M 5/1626* (2013.01); *A61M 5/3273* (2013.01); *A61M 25/0097* (2013.01); *A61M 25/0606* (2013.01); *A61M 25/0618* (2013.01); *A61M 25/0625* (2013.01); *A61M 25/0631* (2013.01); *A61M 2005/325* (2013.01)

(58) Field of Classification Search
CPC ............ A61M 25/0625; A61M 5/3245; A61M 25/0618; A61M 5/3205; A61M 5/150633; A61M 2005/325
See application file for complete search history.

(56) References Cited

U.S. PATENT DOCUMENTS

| | | |
|---|---|---|
| 8,496,623 B2 | 7/2013 | Burkholz |
| 2003/0060774 A1 | 3/2003 | Woehr et al. |
| 2004/0049163 A1 | 3/2004 | Murashita |
| 2009/0163861 A1 | 6/2009 | Carlyon |
| 2010/0222746 A1 | 9/2010 | Burkholz |
| 2011/0301551 A1 | 12/2011 | Koehler et al. |

FOREIGN PATENT DOCUMENTS

| | | |
|---|---|---|
| EP | 1920796 A1 | 5/2008 |
| WO | 9908742 A1 | 2/1999 |
| WO | 2011129753 A1 | 10/2011 |

OTHER PUBLICATIONS

English Translation of Office Action in corresponding Japanese Patent Application No. 2015-529928, dated May 31, 2016.
English Translation of Office Action in corresponding Japanese Patent Application No. 2015-129812, dated Jun. 14, 2016.

*Primary Examiner* — Bradley J Osinski
(74) *Attorney, Agent, or Firm* — Edell, Shapiro & Finnan, LLC

(57) ABSTRACT

A needle guard assembly having a resilient arm extending from a base. In one implementation the needle guard has an elongate containment member that rides with the resilient arm and is co-operable with the resilient arm to effectuate a covering of the entire distal tip of the needle upon the needle being retracted into the elongate containment member.

20 Claims, 14 Drawing Sheets

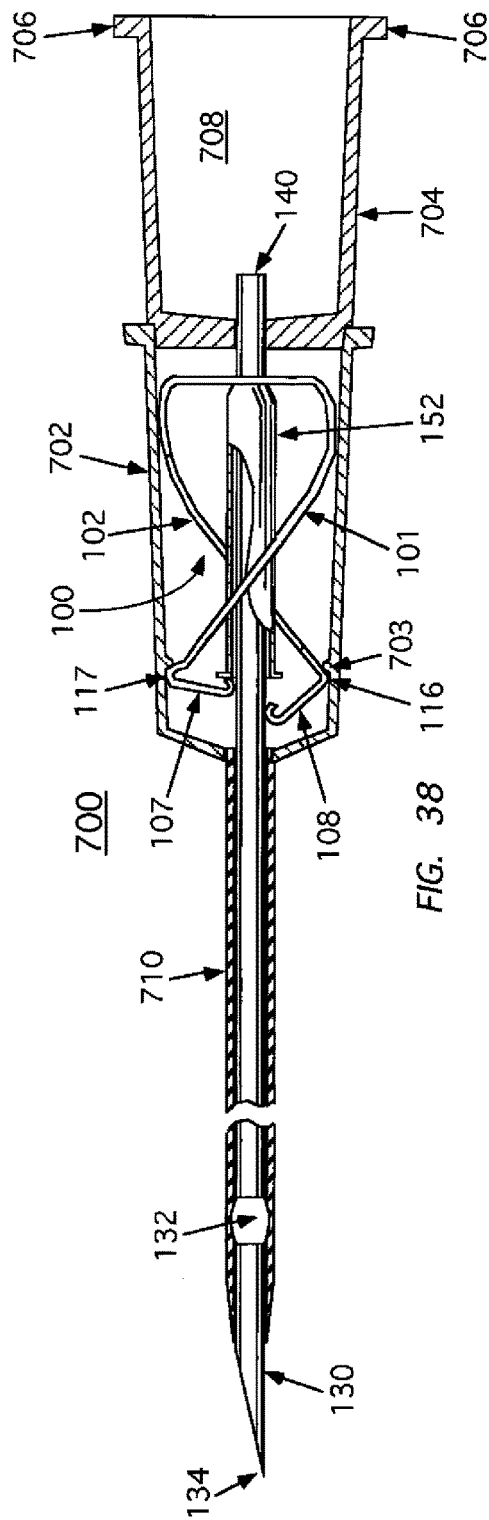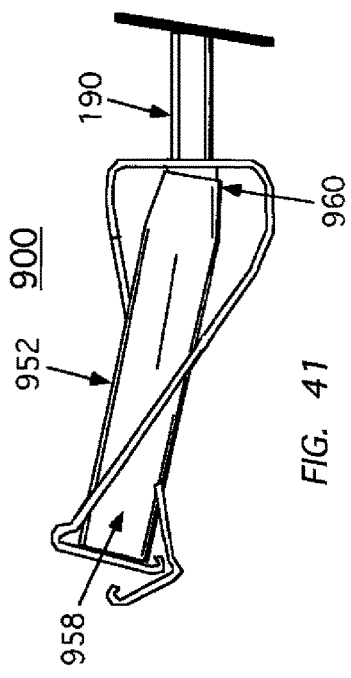
FIG. 38
FIG. 41

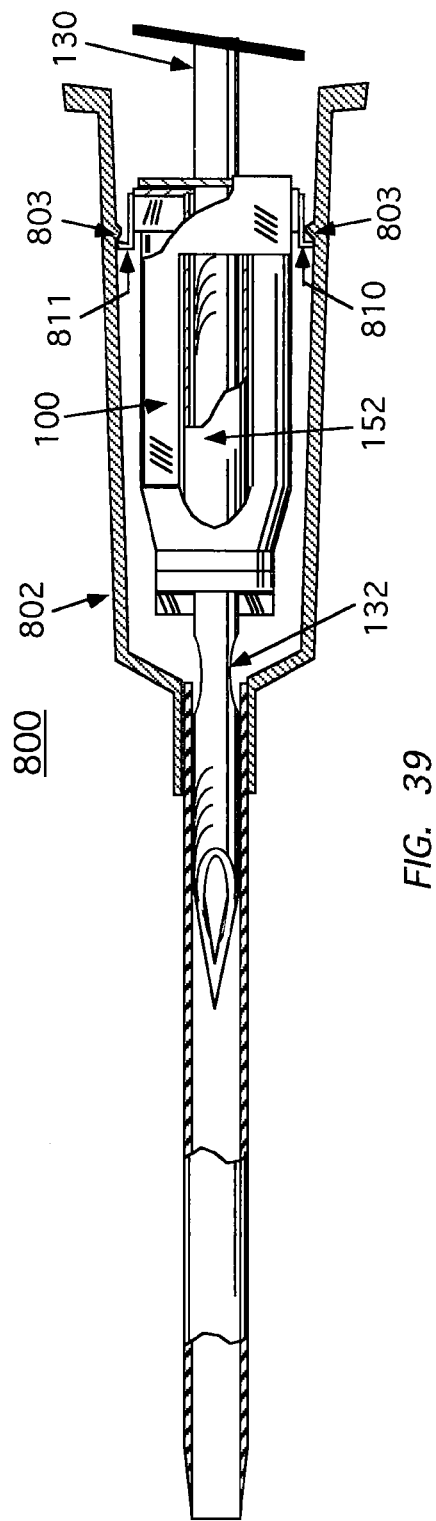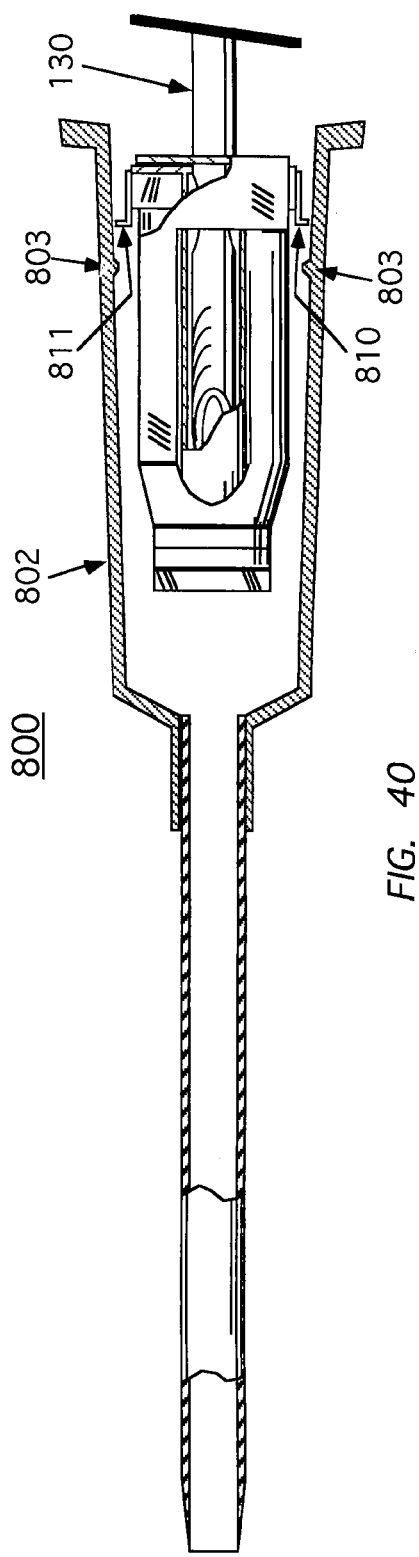
FIG. 39
FIG. 40

NEEDLE GUARD

CROSS-REFERENCE TO RELATED APPLICATIONS

This application is a Continuation of U.S. application Ser. No. 15/010,705, filed Jan. 29, 2016, which is a Continuation of U.S. application Ser. No. 14/247,986, filed Apr. 8, 2014, which is a Continuation of U.S. application Ser. No. 13/037,164 filed Feb. 28, 2011, the disclosures of all of which are incorporated herein by reference.

FIELD

The inventions disclosed herein relate to safety needle devices.

BACKGROUND

A number of U.S. Patents describe safety IV catheters where the distal tip of the needle is provided with a degree of protection after use, including but not limited to: McLees, U.S. Pat. No. 5,135,504; Erskine, U.S. Pat. No. 5,797,880; Woehr, et al., U.S. Pat. No. 6,287,278; Bialecki, et al., U.S. Pat. No. 6,652,486; McGurk, U.S. Pat. No. 7,291,130; Rhad, et al., U.S. Pat. No. 7,303,548; Menzi, et al., U.S. Pat. No. 7,731,687; and Harding, et al., U.S. Pat. No. 7,828,774.

These prior art safety catheters all exhibit one or more drawbacks that could potentially place healthcare workers, or others at risk for a percutaneous or non-percutaneous blood or bodily fluids exposure after the needle tip is covered by the safety mechanism. Although the needle tip itself is covered after use on a number of available safety IV catheters, the entirety of the needle tip is not fully contained after use which could result in blood or fluid residing in the distal end of the needle lumen leaking, or otherwise escaping, into the workplace and contacting a healthcare provider. For example, splattered blood could enter a mucous membrane region of the eyes, nose or mouth of any healthcare personnel within close proximity to the splatter. The exposure should then be reported and post exposure treatment, prophylaxis and follow up would occur, incurring costs to the institution and worry to the individual exposed to the blood. Additionally, some commercially available needle guards can be easily defeated by an inadvertent incident where the components no longer protect or shield the contaminated tip.

FIGS. 1-5 illustrate a safety needle guard 10 similar to the one disclosed in U.S. Pat. No. 6,287,278. The needle guard 10 is constructed from a single piece of material as shown in FIG. 1 and formed to assume the configurations depicted in FIGS. 2-5 during use. FIGS. 2 and 3 show different side views of the needle guard 10 in a ready position where the distal tip 18 of the needle 15 is unprotected. FIGS. 4 and 5 show the different side views of the needle guard 10 after the needle guard has been activated to cover the distal tip 18. As shown in FIGS. 4 and 5, although the extreme distal tip 18 of needle 15 is protected, the open lumen 17 in the bevel region 16 of the needle remains exposed. Another problem associated with the needle guard 10 is that forces may be applied to the needle guard arms 11 and 12 at locations to cause the distal arm segments 13 and 14 to be urged outward. This creates a risk of having the distal arm segments 13 and/or 14 being moved away from protecting the distal tip 18.

SUMMARY

According to some implementations an intravenous (IV) catheter assembly is provided comprising: a catheter hub comprising a hollow body having a proximal end and a distal end, the hollow body defining an interior space; a catheter having a proximal end and a distal end, the proximal end of the catheter coupled to the proximal end of the catheter hub; a needle having a needle shaft and a distal tip, the needle moveable between a ready position and a retracted position, in the ready position the distal tip of the needle extending distally from the distal end of the catheter, in the retracted position the distal tip of the needle residing in a position proximal to the proximal end of the catheter, the needle shaft having a change in profile; and a needle guard comprising an arm that extends distally from a base having an aperture formed therein, the needle guard slideably mounted on the needle shaft with the needle shaft passing through the aperture formed in the base, the aperture sized to engage with the change in profile of the needle shaft to limit the proximal movement of the needle with respect to the needle guard, the arm comprising a resilient material and having a proximal section, a mid-section and a distal section, the distal section of the arm resides and is urged against a side of the needle shaft when the needle is in the ready position, the needle guard further comprising an elongate member having a through passage extending between a proximal end and a distal end of the elongate member, the elongate member extending distally from a position at or near the base and slideable along the needle shaft as the needle is moved between the ready position and the retracted position, the elongate member having a length such that substantially coincident with the change in profile engaging the aperture in the base the entirety of the distal tip of the needle is positioned to reside within the through passage of the elongate member and the distal section of the arm disengage with the needle shaft to move radially inward to at least partially cover the distal end of the elongate member, the elongate member being sufficiently rigid to restrict longitudinal movement of the needle with respect to the needle guard when the distal section of the arm at least partially covers the distal end of the elongate member.

According to other implementations an IV catheter assembly is provided comprising: a catheter hub comprising a hollow body having a proximal end and a distal end, the hollow body defining an interior space; a catheter having a proximal end and a distal end, the proximal end of the catheter coupled to the proximal end of the catheter hub; a needle having a needle shaft and a distal tip, the needle moveable between a ready position and a retracted position, in the ready position the distal tip of the needle extending distally from the distal end of the catheter, in the retracted position the distal tip of the needle residing in a position proximal to the proximal end of the catheter, the needle shaft having a change in profile; and a needle guard comprising first and second arms that extend distally from a base having an aperture formed therein, the needle guard slideably mounted on the needle shaft with the needle shaft passing through the aperture formed in the base, the aperture sized to engage with the change in profile of the needle shaft to limit the proximal movement of the needle with respect to the needle guard, each of the first and second arms comprising a resilient material and having a proximal section, a mid-section and a distal section, the first and second arms extending from different positions of the base and intersecting one another along their mid-sections so that the distal sections of the first and second arms reside and are urged against opposite sides of the needle shaft when the needle is in the ready position, the needle guard further comprising an elongate member having a through passage extending between a proximal end and a distal end of the elongate member, the elongate member extending distally from a position at or near the base and slideable along the needle shaft as the needle is moved between the ready position and the retracted position, the elongate member having a length such that substantially coincident with the change in profile engaging the aperture in the base the entirety of the distal tip of the needle is positioned to reside within the through passage of the elongate member and the distal section of at least one of the first and second arms disengages with the needle shaft and moves radially inward to at least partially cover the distal end of the elongate member, the elongate member being sufficiently rigid to restrict longitudinal movement of the needle with respect to the needle guard when the distal section of at least one of the first and second arms at least partially covers the distal end of the elongate member.

According to some implementations the needle guard comprises a unitary structure with the elongate member being integrally formed with the base of the needle guard.

According to some implementations the needle is stopped in the retracted position by component or feature incorporated with, or otherwise situated, at or near the distal end of the elongate member.

According to some implementations a proximal section of the elongate member comprises a reduced diameter portion and/or a frustoconical portion useable to assist in self-centering the needle on the needle guard.

Many other implementations are disclosed and contemplated herein. Moreover, it is important to note that the inventions are not limited to safety IV catheters, but are applicable to any of a variety of needle products.

BRIEF DESCRIPTION OF THE DRAWINGS

FIG. 38 illustrates a safety intravenous catheter assembly according to one implementation:

FIGS. 39 and 40 illustrate a safety intravenous catheter assembly according to another implementation:

FIG. 41 illustrates a needle guard assembly according to another implementation.

DETAILED DESCRIPTION

Figure 1:
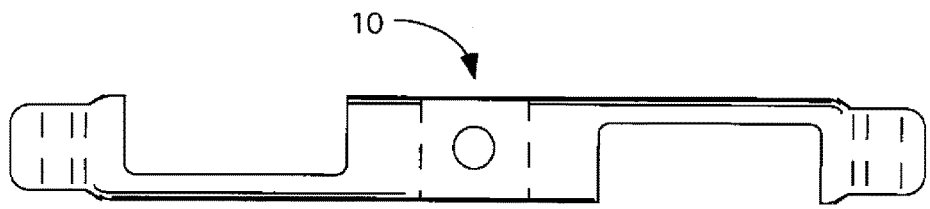
FIGS. 1 through 5 illustrate a prior art needle guard.
Figure 2:
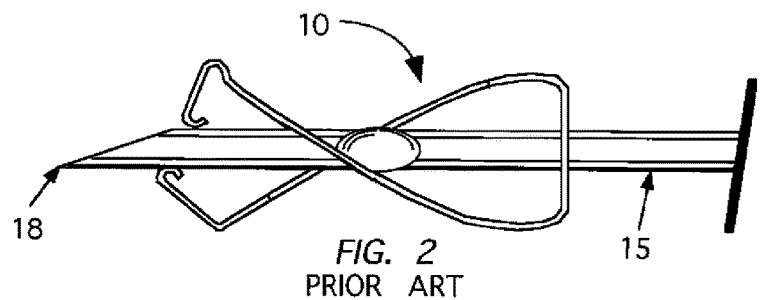
Figure 3:
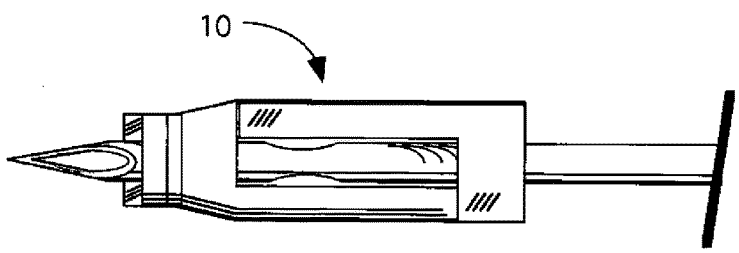
Figure 4:
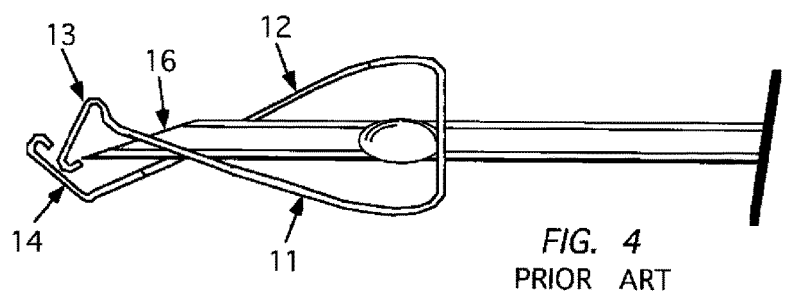
Figure 5:
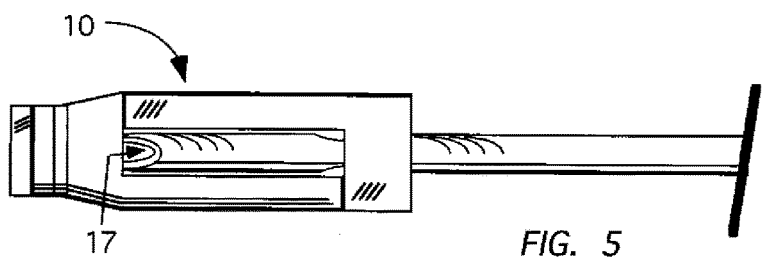
Figure 6A:
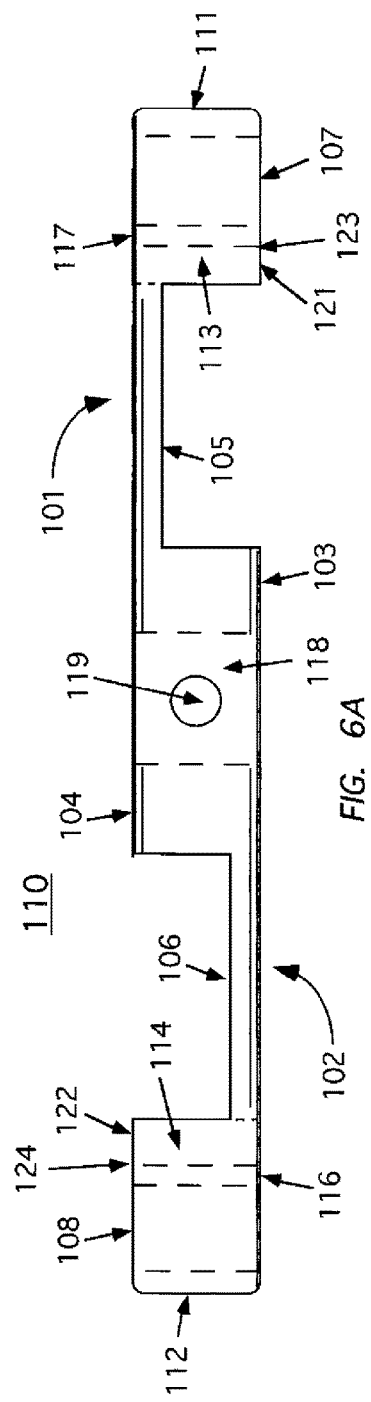
FIGS. 6A through 6C illustrate implementations of a flat stock usable to form needle guards disclosed and contemplated herein.
Figure 6B:
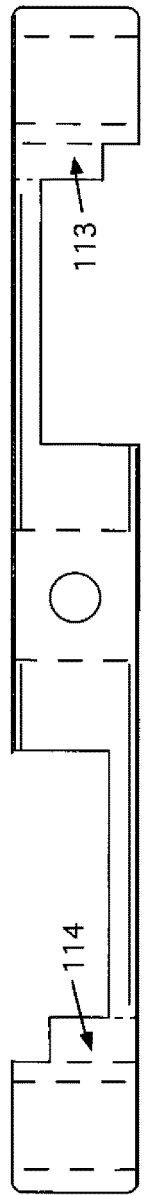
Figure 6C:
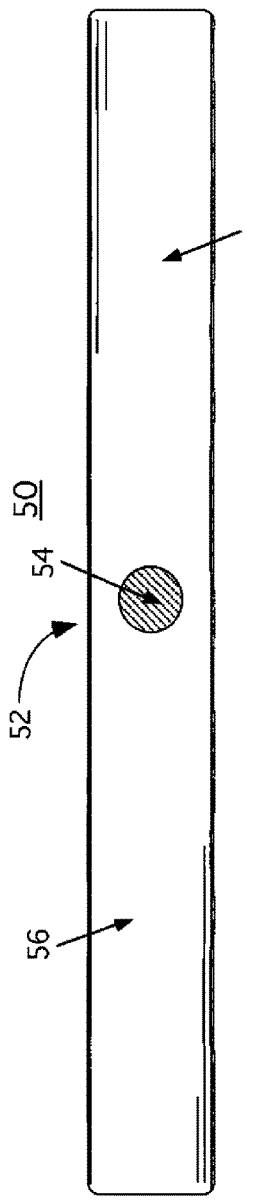
Figure 7:
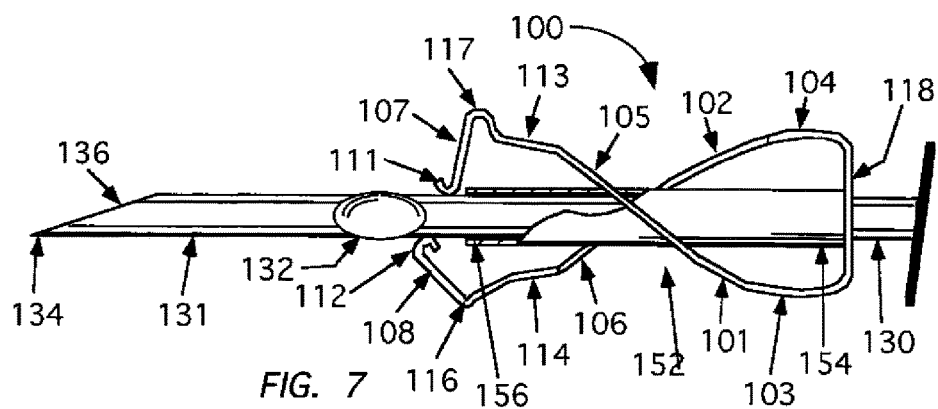
FIGS. 7 through 10 illustrate a needle guard assembly according to one implementation.
Figure 8:
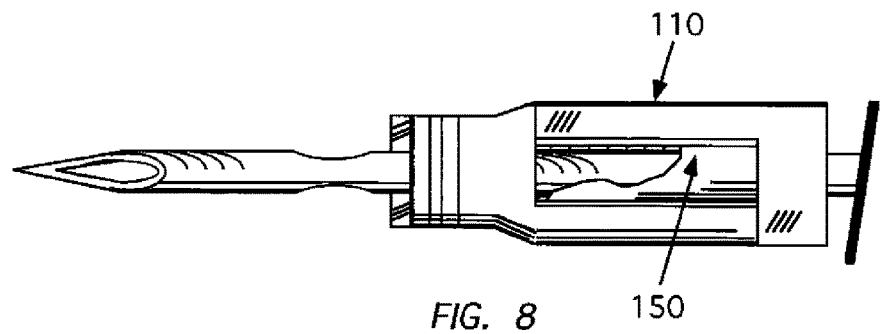
Figure 9:
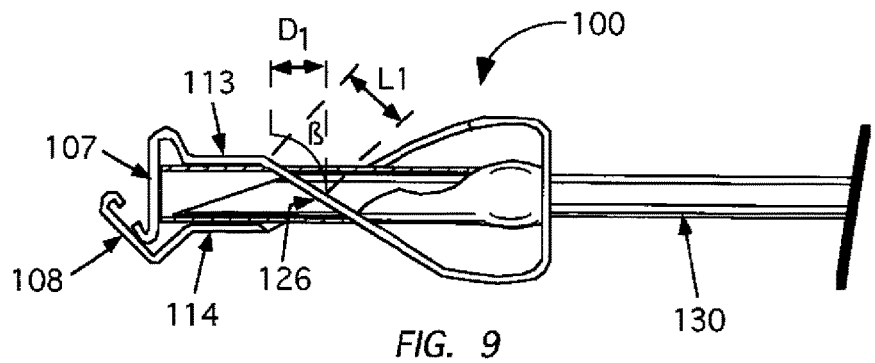
Figure 10:
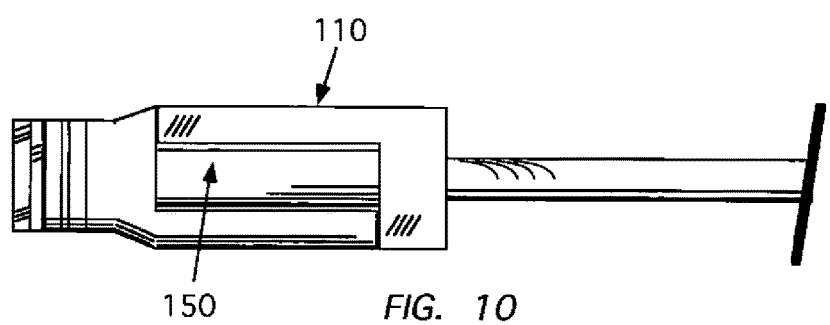
Figure 11:
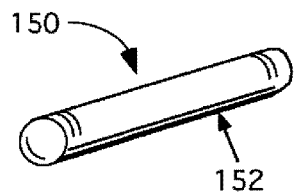
FIGS. 11 through 17 illustrate protective elongate members according to various implementations.
Figure 12:
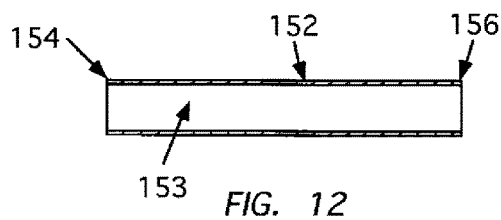

FIGS. 6 through 11 illustrate needle guards 100 according to some implementation. According to one implementation, a first portion 110 of the needle guard 100 is manufactured from a flat material having resilient characteristics, as shown in FIG. 6A or 6B, and shaped to assume the in-use configurations shown in FIGS. 7-10, whereas a second portion 150 (see FIGS. 11 and 12) of the needle guard 100 defines an elongate member 152 having a through passage 153 extending between a proximal end 154 and an distal end 156. FIGS. 7 and 8 show different side views of the needle guard 100 situated in a first axial position on a needle 130 with the distal end 134 of the needle being unprotected. FIGS. 9 and 10 show the different side views with the needle guard 100 situated in a second axial position on the needle 130 with the distal end 134, including the entirety of the bevel 136, being protected.

In one implementation, the first portion 110 of the needle guard 100 has first and second resilient arms 101 and 102, respectively, with each of the arms comprising a proximal section 103,104, a mid-section 105, 106 and a distal section 107, 108. The first and second arms 101, 102 extend distally from different positions of a base 118 and intersect one another along their mid-sections 105, 106 so that lip segments 111, 112 of the distal sections 107, 108 reside at and are urged against opposite sides of the needle shaft 131 when the needle guard is situated in the first axial position. The first portion 110 of the needle guard 100 is slideably mounted on the needle shaft 131 with the needle shaft passing through an aperture 119 formed in the base 118. In one implementation the aperture 119 is sized to engage with a change in profile 132 on the needle to limit movement between the needle 130 and the needle guard 100 in a first direction when the needle guard 100 is situated in the second axial position. The change in profile 132 may comprises a crimp on the needle shaft 131 or any other form of enlargement such as those depicted in FIGS. 33 and 35.

As shown in FIG. 7, the elongate member 152 is situated in the needle guard 100 with its proximal end 154 positioned at or near the base 118, and with its distal end 156 positioned at or near lip segment 111 of arm 101 when the needle guard is in the ready position. In some implementations the elongate member 152 is substantially coaxial with the needle 130 with the diameter or cross-sectional area of the through passage 153 being sufficiently large to permit the elongate member to slide over the change in profile 132. In other implementations the elongate member 152 is substantially coaxial with the needle 130 with the diameter or cross-sectional area of all or a proximal portion of the through passage 153 being smaller than a cross-sectional area of the change in profile 132. In implementations where all or a portion of the through passage 153 has a cross-sectional area smaller than a cross-sectional area of the change in profile 132, the through passage 153 is made to be expandable over the change in profile 132, like, for example that shown in FIG. 9. In some implementations the sections of the elongate member 152 where the through passage 153 has a smaller cross-sectional area than the change in profile 132 are resilient to cause the cross-sectional area of the through passage 153 to contract inwardly after that portion of the through passage has crossed the change in profile. In some implementations, as discussed in more detail below, only a proximal portion of the expandable member 152 has a reduced cross-sectional area that is resiliently expandable over the change in profile 132. In use, the elongate member 152 travels axially along the shaft of the needle in conjunction with the first portion 110 of the needle guard 100. In some implementations the elongate member 152 rides with the first portion 110 of the needle guard with the proximal end 154 abutting the base 118. In other implementations the proximal end 154 of the elongate member 152 is attached to base 118. In other implementations, a proximal portion or all of the elongate member 152 is integral with the base 118.

FIGS. 9 and 10 show the needle guard 100 positioned on the needle 130 in the second axial position with the needle tip 134, including the entirety of the bevel 136, being covered. In one implementation, as the needle guard is advanced over the needle 130 and the lip segments 111 and 112 are moved distal to the needle tip 134, the needle guard 100 is stopped in the second axial position by the engagement of the change in profile 132 on the needle with the aperture 119 of base 118. Other stop implementations are disclosed below. The length of the elongate member 152 is selected so that substantially coincident with the change in profile 132 engaging, for example, the aperture 119 in base 118 the entirety of the distal tip 134 and bevel region 136 of needle 130 is positioned to reside within the through passage 153 and so that at least one of the distal sections 107, 108 of arms 101, 102 disengage with the needle to fully or at least partially cover the distal end 156 of the elongate member 152.

In one implementation, as shown in FIG. 7, the distal section 107 of arm 101 is configured to assume a first angle with respect to the needle axis when the needle guard 100 is positioned in a ready position and the distal section 108 of arm 102 is configured to assume a second angle with respect to the needle axis when the needle guard 100 is positioned in the ready position, the second angle being greater than the first angle. Further, as shown in FIG. 9, when the needle guard 100 is in the second axial position the distal section 107 of arm 101 is oriented and biased to assume a substantially perpendicular relationship with respect to the longitudinal axis of the elongate member 152. In some implementations the cross-sectional area of the distal section 107 is sufficient to cover the entirety of the distal end 156 of the elongate member 152. In other implementations, less than the entirety of the distal end 156 of the elongate member 152 is covered by distal section 107.

As mentioned above, the distal end 107 of arm 101 may be biased so that it applies a downward/proximally acting force on the distal end 156 of elongate member 152 when the needle guard 100 assumes the second axial position. In one implementation the bias is created by a resilient hinge in the region 117. The application of a downward/proximally acting force assists in the formation of a full or partial seal that may impede or prevent contaminants within the needle 130 and elongate member 152 lumens from leaking out of the needle guard 100 after it has assumed the second axial position. In some implementations, the distal end 108 of arm 102 is oriented and biased to assume an oblique angle with respect to the distal end 107 and to exert a force on the distal end 107 in a direction toward the distal end 156 of elongate member 152.

In implementations where the needle guard 100 forms a part of an intravnous catheter 700, as shown in FIG. 38, protrusions 117 and 116 may be formed on arms 101 and 102, respectively, to engage with one or more features 703 in the interior of the catheter hub 702 to releasably secure the needle guard 100 in the catheter hub when the catheter assembly 700 is in a ready position.

As mentioned above, a problem associated with prior art spring clip needle guard devices is that forces may be applied to parts of the spring clip arms to cause the distal arm sections to be urged outward. This creates a risk of the distal arm sections being moved away from protecting the needle tip after the needle guard has assumed a protected position. To address the problem, in some implementations the first portion 110 of the needle guard 100 comprises straight, or substantially straight, arm segments 113 and 114 that are disposed proximal to distal arm sections 107 and 108, respectively. As shown in FIG. 9, the arm segments 113 and 114 are arranged so that when the needle guard 100 assumes the second axial position on the needle 130, the arms segments 113 and 114 abut and are laterally disposed on opposite sides of the outer surface of the elongate member 152. Arm segments 113 and 114 are disposed to occupy positions between the distal sections 107, 108 and the intersection point 126 of the arms 101 and 102 when the needle guard is in the second axial position. In one implementation arm segments 113 and 114 are located adjacent to distal sections 107 and 108, respectively, and disposed a distance distal to the intersection point 126 of the arms 101 and 102. In one implementation the distance ($D_1$) segment 113 is distally spaced from the intersection point 126 is greater than or equal to $L_1 \sin \beta$, with L1 being the approximate distance between the intersection point 126 and the location arm 101 intersects the outer circumference of the elongate member 152 and $\beta$ being the angle between arm 101 and a line running perpendicular to the longitudinal axis of elongate member 152 at the intersection point 126. Although not required, segment 114 is preferably distally spaced from the intersection point 126 so to be substantially longitudinally aligned with segment 113.

In some implementations segments 113 and 114 have substantially the same width as distal sections 107 and 108, respectively. In other implementations segments 113 and 114 have widths that are less than those of distal sections 107 and 108, respectively, as shown in FIG. 6B. In other implementations, one or both of segments 113 and 114 may comprise arcuate portions that at least partially conform to portions of the outer curvature of the elongate member 152. An advantage of such a configuration is that the at least partial conformability of segments 113, 114 with the outer surface of elongate member 152 acts to stabilize the segments about the elongate member in the event improper forces are applied to either or both of arms 101 and 102. In other words, the at least partial conformability reduces the likelihood of arms 101 and/or 102 slipping sideways on the outer surface of elongate member 152 when improper forces are applied to arms 101 and/or 102. As an example, and with reference to FIG. 6A, the outer edges 121 and 122 of segments 113 and 114 may be curved inward along cut-lines 123 and 124, respectively, to assume a partially curved configuration.

The first portion 110 and second portion 150 of the needle guard 100 may assume any of a variety of configurations. Turning again to FIGS. 6A and 6B, in one implementation the arm mid-sections 105 and 106 are narrowed sufficiently to accommodate the elongate member 152 with a clearance existing between the mid-sections 105 and 106 and the outer surface of the elongate member when the first portion 110 is formed into a spring clip as exemplified in FIGS. 7-10. The dotted lines in FIGS. 6A and 6B depict folding locations for producing bends and/or hinges during the spring clip fabrication process.

In some implementations the elongate member 152 comprises one or more materials having sufficient rigidity to resist buckling during use. The one or more materials may comprise any of a variety or composition of materials, such as for example, a metal, an elastomer/plastic, a braided structure, a random stranded structure, combinations thereof, etc. Elongate member 152 may comprise a plurality of portions or sections joined together to form the elongate member.

Elongate member 152 may be fabricated, for example, utilizing a deep-draw fabrication process where a metal is work hardened during the drawing process, thus eliminating the need for secondary heat-treating on the finished part. Elongate member 152 may also comprise, for example, an extruded portion of elastomer/plastic tubing.

According to some implementations, the through passage 153 in a proximal portion of the elongate member 152 adjacent or near the base 118 has a reduced cross-sectional area/diameter that causes the proximal portion of the through passage 153 to engage with the change in profile 132 on the needle shaft 131. In one implementation the reduced diameter portion of the through passage 153 acts as stop, in lieu of aperture 119 in base 118, to limit movement of the needle guard 100 on the needle 130 to the second axial position. In other implementations a reduced diameter bushing or sleeve may be positioned at or coupled with the proximal end 154 of the elongate member 152 to act as a stop.

According to other implementations, the proximal portion of the elongate member 152 comprises a material that is capable of expanding or flexing over the change in profile 132 in a manner depicted in FIG. 9. In one implementation the proximal portion of the elongate member comprises a resilient material that permits it to expand over the change in profile 132 while at the same time exerting a constraining/radial force on the change in profile 132. An advantage of such implementations is that the radial constraining force applied to the change in profile 132 acts to limit lateral movement of the elongate member 152 after the needle guard 100 has been positioned to cover the distal end of the needle. This is particularly advantageous when a full or partial seal between the distal section 107 or arm 101 and the distal end 156 of elongate member 152 is desired. According to other implementations the entirety of elongate member 152 comprises a flexible material that allows the elongate member to expand or flex over change in profile 132 of the needle 130 as the elongate member is slid or moved to the distal end of the needle.

Figure 13:
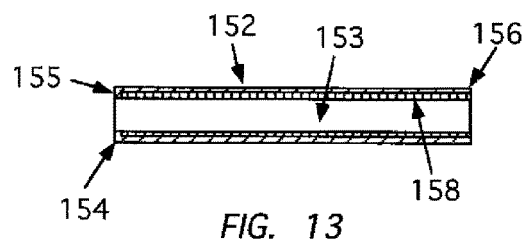

FIG. 13 is a cross sectional side view of an implementation of elongate member 152 having a reduced inner diameter proximal portion 155. The elongate member 152 may also have an absorbent or porous inner coating/membrane/liner or the like 158 sized to contact the outer diameter of needle 130 and absorb or wipe blood or bodily fluids from the exterior surface of the needle as the needle slides or moves through the elongate member. The absorbent or porous member 158 may also absorb blood or bodily fluids that reside in the needle lumen. In some implementations the absorbent or porous member 158 includes a medication, such as, for example, an antimicrobial or antibiotic agent.

Figure 14:
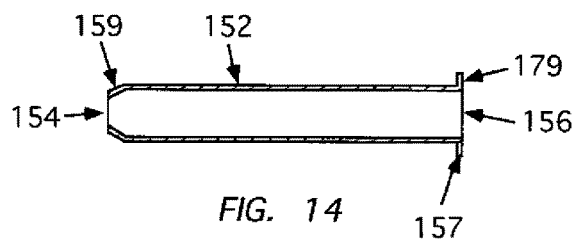

FIG. 14 is a cross sectional side view of an implementation of elongate member 152 comprising a reduced diameter or frustoconical portion 159 at its proximal end 154 and a distal flange 157 at its distal end 156. According to one implementation the distal flange 157 provides a larger contacting surface 179 to facilitate the formation of a seal between the distal section 107 of arm 101 and the distal end 156 of the elongate member when the needle guard is positioned in the second axial position on the needle 130. In other implementations the distal flange 157 and the lip 111 of arm 101 are constructed so that upon the needle guard 100 assuming the second axial position on the needle 130 the lip 111 engages with the flange 157 to help secure the distal section 107 of arm 101 to the distal end 156 of elongate member 152. In such implementations, the distal flange 157 may be annular, continuous or segmented.

Figure 15:
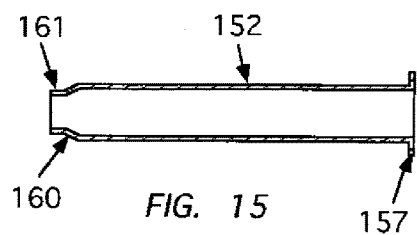

FIG. 15 is a cross sectional view of an implementation of elongate member 152 comprising a proximal section having a reduced diameter or frustoconical portion 160 transitioning to a reduced diameter end section or sleeve 161. The elongate member 152 may also comprise a distal flange 157. In one implementation the proximal end section 161 is used for attaching the proximal end of the elongate member 152 to the base 118. Attachment may be accomplished via stamping, pressing or other mechanical fastening processes. For example, the proximal section 161 may be segmented to form tabs, or the like) that are fixed into aperture 119 or other openings provided in the base 118. In other implementations the shape and size of the proximal section 161 permits it to be press fitted into aperture 119. It is important to note that any of a variety of other attachment methods, or combination of methods, may be used to attach the elongate members 152 disclosed and contemplated herein to the base 118 of the needle guard. These methods may include the use of adhesives, soldering, welding, mechanical attachment, etc. As will be discussed in more detail below, in some implementations the elongate member 152 is unitarily formed with the first portion 110 of the needle guard 100.

An advantage of providing areas/sections of reduced diameter along a length of the elongate member 152 is that these areas/sections assist in maintaining the elongate member coaxially disposed on the needle 130 which reduces friction or drag forces that may otherwise exist as the elongate member 152 is moved along the needle shaft 131. They also assist in urging or maintaining the elongate member 152 in a coaxial relationship with the needle shaft 131.

Figure 16:
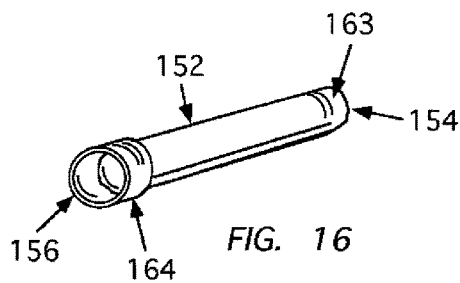
Figure 17:

FIG. 16 is an isometric view of an implementation of an elongate member 152 having an enlarged diameter distal portion 164 and a small diameter proximal portion 163. FIG. 17 is a cross sectional view of one implementation of an elongate member according to FIG. 16 comprising an inner ring or bushing 165 retained within the cavity of the enlarged diameter portion 164 that is situated to concentrically locate the needle 130 within the elongate member 152 and to wipe blood or bodily fluids from the exterior surface of the needle 130 as the needle slides or axially moves through the elongate member 152. One advantage of the enlarged diameter distal portion 164 is that it provides a reservoir for collecting blood or bodily fluids wiped from the exterior surface of the needle and/or that emanate from the lumen of the needle. In one implementation the reservoir contains a coating or material for absorbing the blood or bodily fluids. In one implementation the absorbent material occupies all or a substantial portion of the reservoir and is deformable or pierceable to accommodate an introduction of the distal end of the needle into the reservoir region of the elongate member. In implementations where a seal is provided between the distal end of the elongate member and the distal arm section 107, one or more apertures may be provided in the wall of the reservoir to inhibit the formation of a hydraulic lock. In one implementation the one or more apertures in the wall of the reservoir are sufficiently small to prevent or inhibit blood or bodily floods from passing there through.

In some implementations an internal or external sealing member is provided at or near the proximal end 154 of the elongate member.

In other implementations the elongate member 152 comprises one or more encapsulated annular rings, ribs or segments that deform or flex over the change in profile 132 as the needle guard 100 is advanced over the needle 130. In some implementations the elongate member 152 comprises elongate encapsulated portions that extend along all or a portion of the length of the elongate member. In such implementations the encapsulation structures may be formed by use of an extrusion process. The encapsulated members may comprise chemical substances that are caused to interact with one another as the one or more encapsulated members expand over the change in profile 132 and to solidify to lock the proximal end 154 of the elongate member 152 onto the change in profile 132 of the needle 130.

As discussed above, it may be desirable to form a partial or full seal at the intersection of the distal section 107 of arm 101 and the distal end 156 of the elongate member 152 when the needle guard 100 is positioned in the second axial position. According to some implementations, the inner surface of distal section 107 is coated or laminated with a material, compound or agent conducive to forming a seal with the distal end 156 of the elongate member 152 when the distal section 107 comes into contact with distal end 156. Conversely, or in conjunction with coating or laminating the inner surface of distal arm section 107, the distal end 156 of elongate member 152 may also be coated or laminated with a material, compound or agent conducive to forming a seal. For example, in some implementations one or both of distal section 107 and distal end 156 comprise a formable material, such as an elastomer, for effectuating a full or partial seal between the members. Other examples include coating, laminating, or otherwise treating one or both of the contact surfaces with a tacky substance or adhesive. Other examples may include the fixation of an elastomer O-ring on the distal end 156 of the elongate member 152 so that at least a portion of the O-ring extends distal to the end 156 so that it may mate with a contact surface of distal arm section 107. Other sealing methods are also contemplated.

Figure 18:
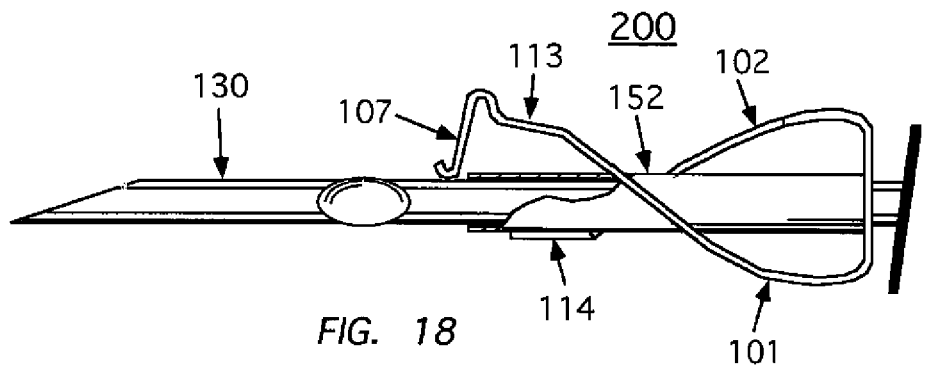
FIGS. 18 and 19 illustrate a needle guard assembly according to another implementation.
Figure 19:
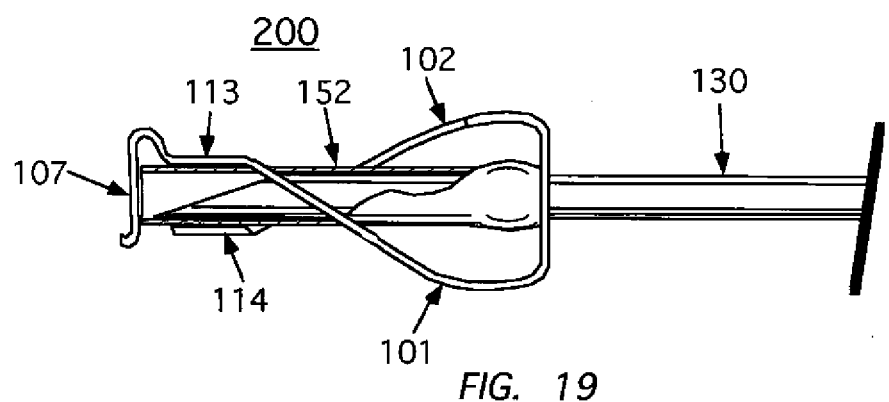

FIGS. 18 and 19 show a needle guard 200 according to another implementation. The needle guard 200 is similar to that of needle guard 100 described above except that arm 102 terminates at segment 114 where it is attached to the outer surface of the elongate member 152. In one implementation, segment 114 is curved to produce an attachment surface that is the same as or approximates the curvature of the outer surface of the elongate member 152. In substantially all other respects the implementations of the first portion 110 and the second portion 150 of the needle guard 200 function in the same way to effectuate a covering of the distal end of the needle 130 as described above. It is important to note that arm 102 may be fixed to the outer surface of the elongate member 152 at more proximally located sites. For example, arm 102 may comprise a shorter length with an end portion of the arm 102 being attached anywhere along the length of the elongate member 152. In other implementations arm 102 is eliminated altogether with the distal end 154 of the elongate member 152 being firmly coupled to the base 118.

According to other implementations the first portion 110 and the elongate member 152 of the needle guard 100 are unitarily constructed. In one implementation this accomplished by subjecting the base 118 of the needle guard to a deep drawing process to form the elongate member 152. In this manner, the elongate member 152 may be described as being co-extensive to the aperture 119 in the base 118. According to one implementation the unitary construction process begins with the formation of a metal strip 50 as shown in FIG. 6C having an area 52 designated to form the base 118 of the needle guard 100. In some implementations the metal strip 50 has a uniform thickness, while in others the strip 50 is provided with an enhanced thickness dimension at least in the region 54 where the deep drawing process is to be applied to form the elongate member 152. In some implementation the arm sections 101 and/or 102, as shown, for example in FIG. 6A, are formed prior to deep drawing the elongate member 152, while in other implementations the arm sections 101 and/or 102 are formed after the formation of the elongate member 152. In some implementations the fabrication process begins with a metal sheet having a uniformed and enhanced thickness dimension which is followed by a process that results in the flattening of the metal sheet in the areas 56 and 58 where the arms 101 and/or 102 are designated to reside. The flattening process may occur before or after the formation of the elongate member 152 by use of the deep drawing process. In conjunction with or after the flattening process to produce one or more areas of a reduced thickness, at least a portion of the reduced thickness areas are cut to produce at least a portion of arms 101 and/or 102.

With reference to FIGS. 13 through 17, one or more of the features 155, 159, 160, 161, 163 and 164 may be formed into the elongate member 152 during the deep drawing process by the use of one or multiple dies dimensioned and shaped to form the one or more features. For example, in one implementation the frustoconical portion 160 and reduced diameter end section 161 of the elongate member 152 is formed during the drawing process. An advantage of incorporating one or both of the features 160 and 161 into the elongate member 152 is that they cause the proximal section of elongate member 152 to be self-centered onto the needle 130 during the assembly process.

According to another manufacturing process, a plurality of elongate members 152 are initially deep drawn, or at least partially deep drawn, from a single metal sheet prior to the metal sheet being segmented for the purpose of forming the first portions 110 of the needle guard 100.

FIGS. 20 through 23 illustrate a needle guard assembly 300 according to another implementation. The needle guard 300 is similar to that of needle guard 100 described above except that arm segments 113 and 114 have been modified to include arcuate recesses 313 and 314 that are configured to at least partially coincide with the curvature of the outer surface of elongate member 152. In one implementation one or both of the recesses 313 and 314 are configured as half-circles that are shaped to coincide with the outer profile of the elongate member 152 when the needle guard 300 is in the second axial position to protect the distal end of needle 130. The circumferential edges of recesses 313 and 314 rest against the outer surface of the elongate member 152 when the needle guard 300 is in the second axial position (FIG. 23) to inhibit the distal sections 107 and 108 of arms 101 and 102 from being urged outward away from covering the distal end of the needle 130 in the event an improper force is applied to one or both of the arms.

Figure 20:
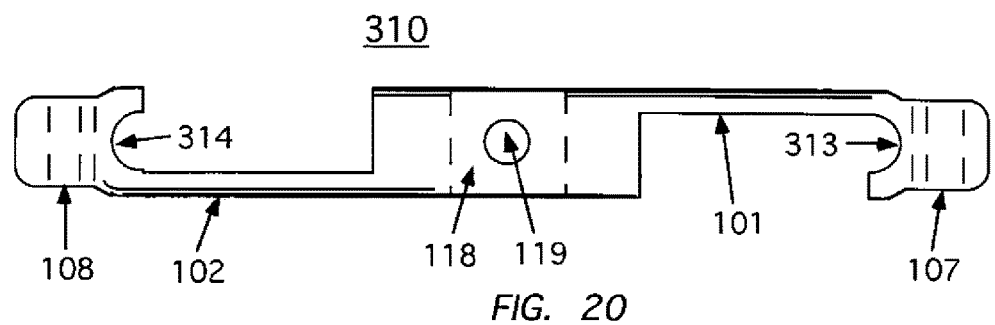
FIGS. 20 through 23 illustrate a needle guard assembly according to another implementation.
Figure 21:
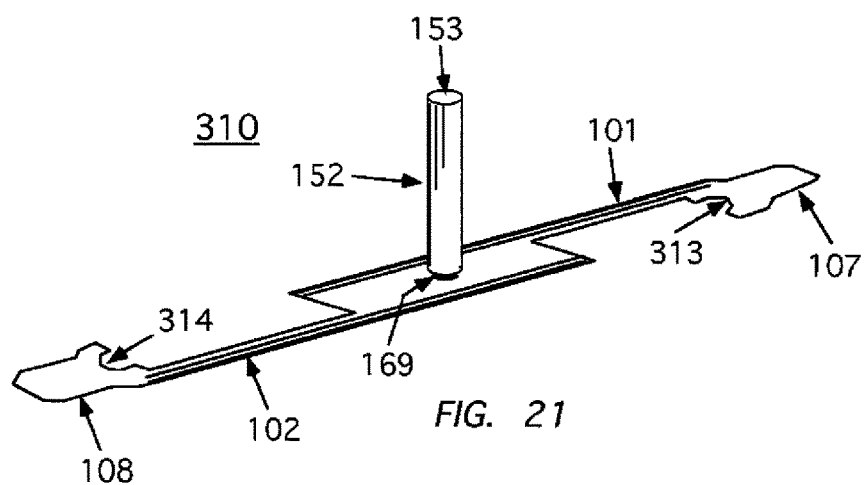
Figure 22:
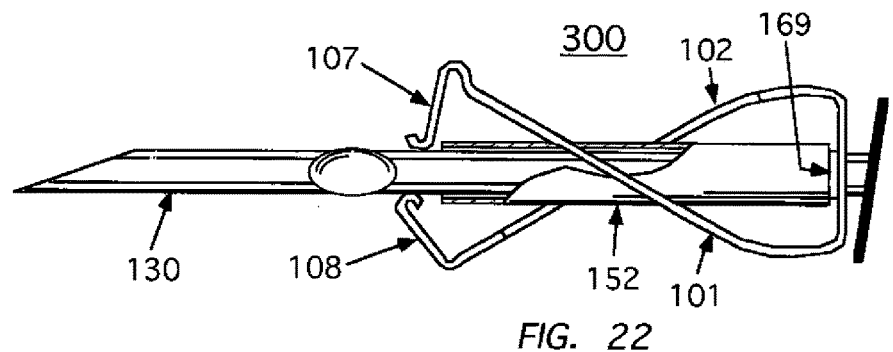
Figure 23:
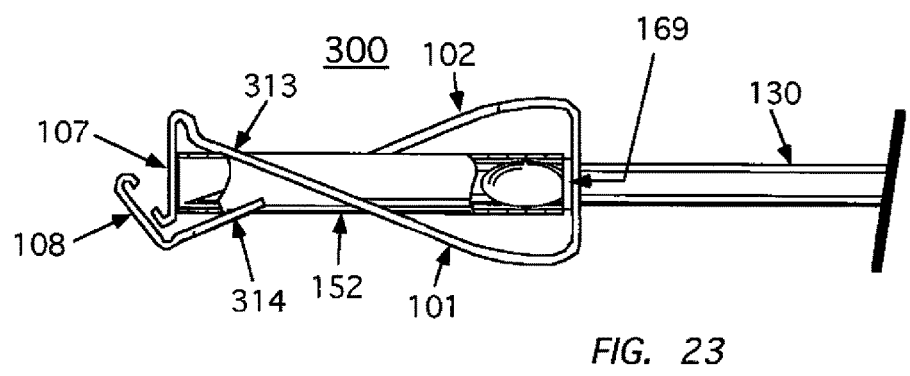

As shown in FIG. 21, a method of fabricating a needle guard according to the implementations disclosed and contemplated herein is to first stamp, cut or otherwise form the first portion 310 of the needle guard from a flat piece of resilient material as exemplified in FIG. 20. After the first portion 310 is formed the elongate member 152 may be positioned so that the through passage 153 is axially aligned with the aperture 119 in base 118. A fixture extending through the aperture 119 and through at least a portion of the through passage 153 may be used to support the elongate member 152. According to other methods, the proximal end 154 of the elongate member 152 is provided with an outer reduced diameter segment 169 that extends through or is otherwise fitted to aperture 119 to fully or partially support the elongate member 152 in a perpendicular relationship with the first portion 310 as shown in FIG. 21. In one implementation, a reduced diameter annular ring located near the proximal end 154 of the elongate member 152 provides a means to snap fit the proximal end of the elongate member into the base aperture 119 to secure the elongate member 152 to the base 118. In other implementations, a slit or slot is provided in the base 118 that extends from a side edge of the base to the aperture 119. In this manner the elongate member 152 may be provided with a reduced diameter annular ring portion near its proximal end 154 that permits the elongate member to be side loaded and fixed within the aperture 119 to effectuate an attachment of the elongate member 152 to the base 118. Upon the elongate member 152 being properly supported on or attached to the first portion 310, the first portion may be bent or partially bent to produce or partially produce the requisite arm portions and hinges. At this stage the first portion 310 and elongate member 152 may be loaded onto the needle 130 with the first portion 310 being further bent (if required) and arranged on the needle 130 in a manner depicted in FIG. 22.

According to some implementations the first portion 310 and elongate member 152 of needle guard 300 are unitarily constructed.

Figure 24:
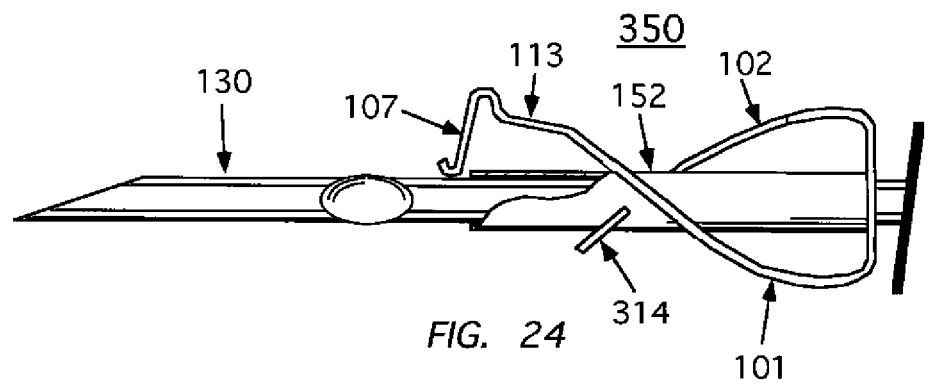
FIG. 24 illustrates a needle guard assembly according to another implementation.

FIG. 24 shows a needle guard 350 according to another implementation. The needle guard 350 is similar to that of needle guard 300 described above except that arm 102 terminates just distal to recess 314 along dotted line 320. In such an implementation the recess portion 314 is continually urged into contact with the outer surface of the elongate member 152 with the distal section 107 of arm 101 situated to singularly cover the distal end 156 of the elongate member when the needle guard 350 is situated in the second axial position on the needle 130. The arms 101 and 102 of needle guards disclosed and contemplated herein may comprise different types of features as exemplified in FIG. 24 where arm 102 is comprises a recess 314 for abutting the outer surface of elongate member 152 and where arm 101 comprises an elongate surface 113 for abutting the outer surface of the elongate member 152.

According to some implementations the first portion and elongate member of the needle guard of FIG. 24 is unitarily constructed.

Figure 25A:
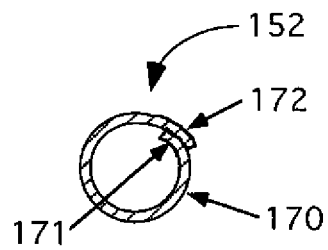
FIGS. 25A-D illustrate needle guard elongate members according various implementations.

According to some implementations, as shown in FIG. 25A, the elongate member 152 comprises a resilient structure 170 having over-lapping longitudinal portions 171 and 172 that are separable to form a temporary longitudinal slit or slot along the length of the elongate member to permit it to be side-loaded onto the needle 130. FIG. 25A represents a top view of the elongate member 152. Upon the elongate member 152 being side-loaded onto the needle shaft, the resilient structure 170 resumes, or substantially resumes, its initial configuration to completely surround the circumference of the needle shaft 131. In one implementation the resilient structure 170 comprises an elastomer material having surface characteristics that facilitate the formation of a seal along the over-lapping longitudinal portions 171 and 172 when their contact surfaces are brought into contact with one another. In other implementations the resilient structure 170 comprises a metal. In some implementations one or both of the over-lapping contact surfaces of portions 171 and 172 is treated or otherwise coated with a substance to induce the formation of a seal along the length of the elongate member 152. In other implementations a seal is formed between the overlapping portions 171 and 172 by use of a sonic welding process or the like.

Figure 25B:
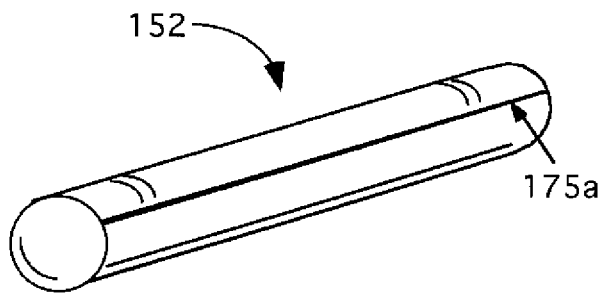
Figure 25C:
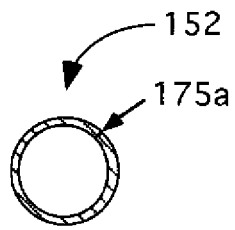
Figure 25D:
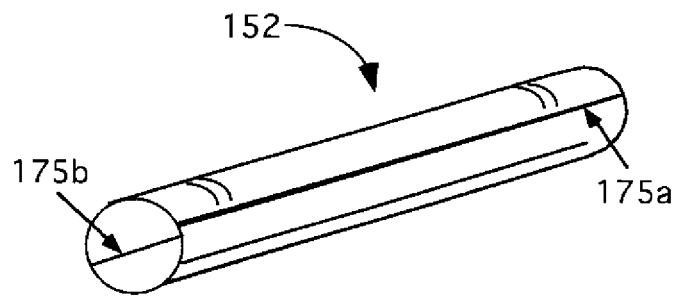
Figure 26:
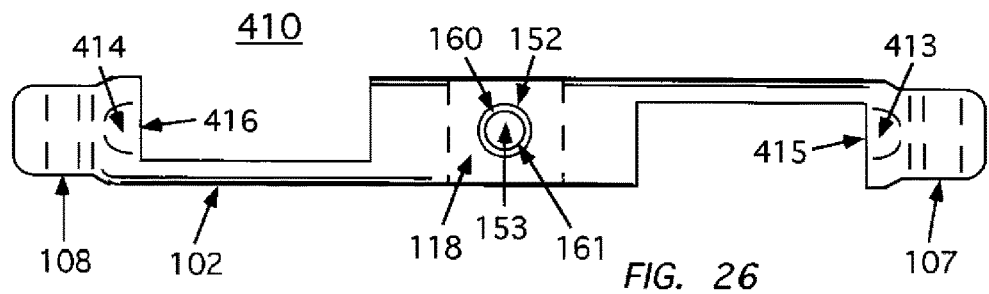
FIGS. 26 through 31 illustrate a needle guard assembly according to another implementation.
Figure 27:
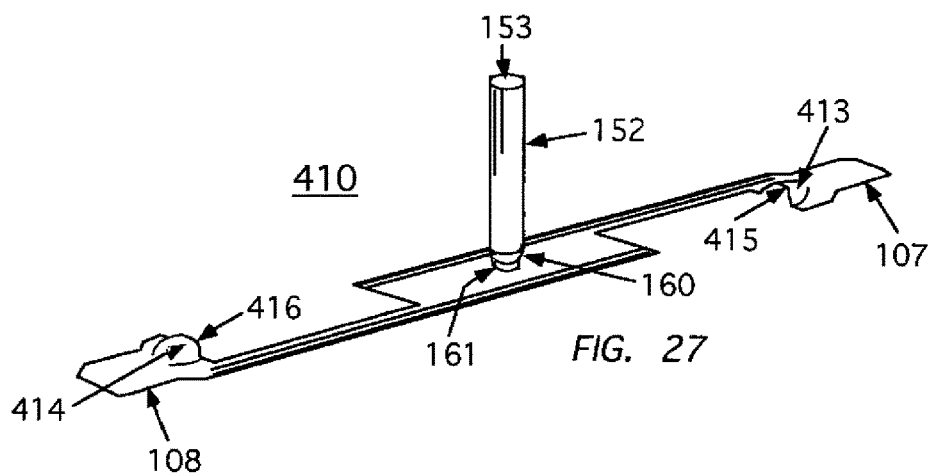
Figure 28:
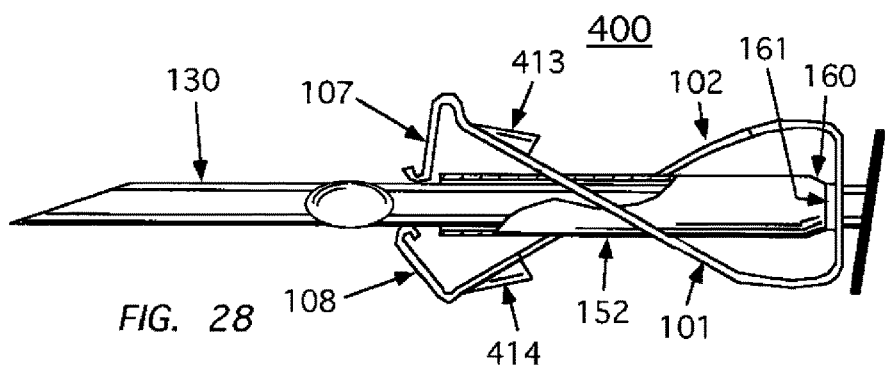

In other implementations, as illustrated in FIGS. 25B-D, the elongate member 152 comprises one or more slits 175a, 175b that are separable to facilitate a side loading of the elongate member onto the shaft of a needle. As with some of the implementations of FIG. 25A, the elongate member 152 may comprise an elastomer material having characteristics that facilitate the formation of a seal between the mating surfaces of the slits when their contact surfaces are brought into contact with one another. In other implementations one or both of the contact surfaces of slits is treated or otherwise coated with a substance to induce the formation of a seal along the length of the elongate member 152. In other implementations a seal is formed between mating surfaces of the slits by use of a sonic welding process or the like.

Figure 29:
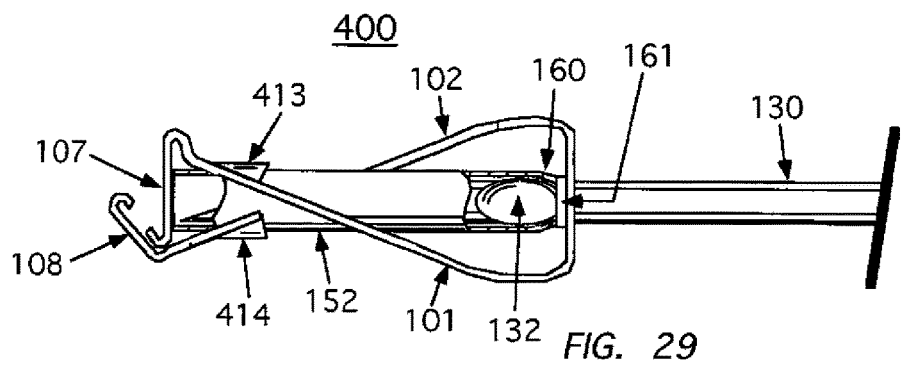
Figure 30:
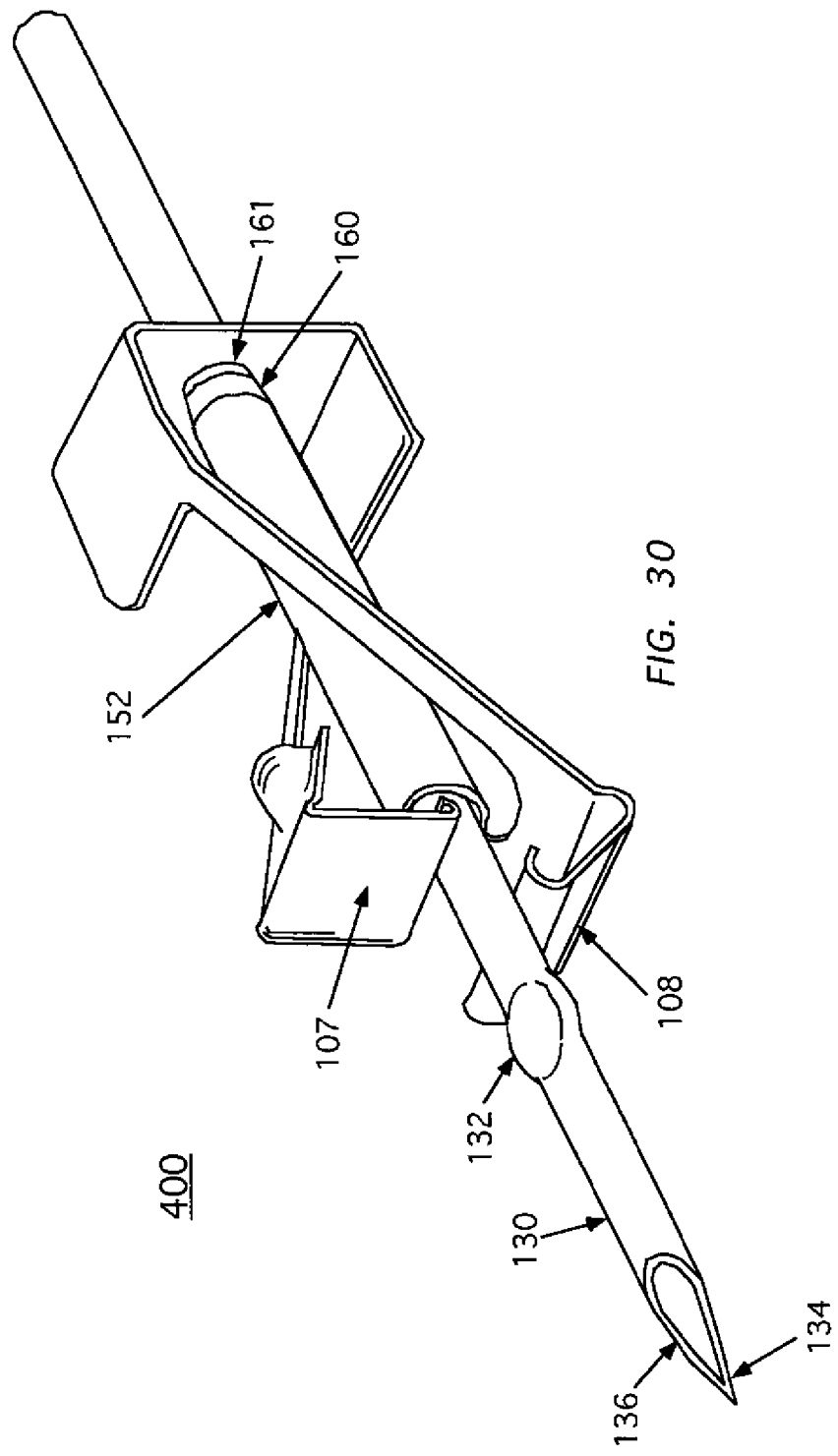
Figure 31:
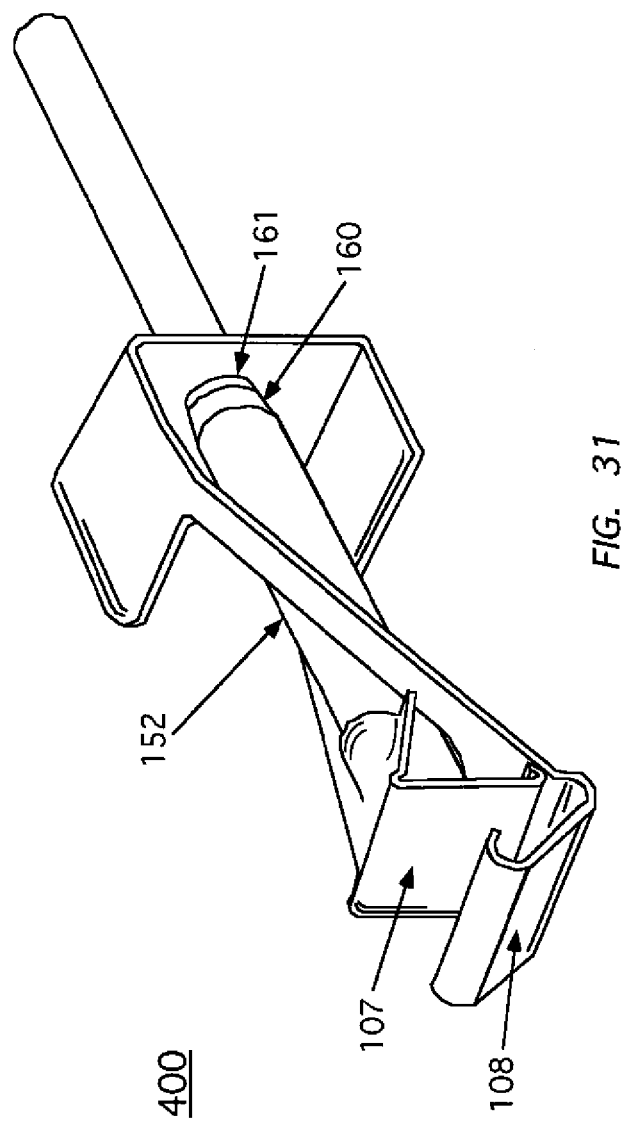

FIGS. 26 through 31 illustrate a needle guard assembly 400 according to another implementation. The needle guard 400 is similar to that of needle guard 100 described above except that arm segments 113 and 114 have been modified to include formed portions 413 and 414 that are configured to at least partially coincide with the curvature of the outer surface of elongate member 152. A proximal section of the elongate member 152 also includes a frustoconical portion 160 and a reduced diameter portion 161 like that depicted in FIG. 15. In one implementation one or both of the proximal edges 415, 416 of formed portions 413, 414 are shaped to coincide with the outer profile of the elongate member 152 when the needle guard 400 is in the second axial position to protect the distal end of needle 130. In practice the inner surfaces of the formed portions 413 and 414 rest against the outer surface of the elongate member 152 when the needle guard 400 is in the second axial position to inhibit the distal sections 107 and 108 of arms 101 and 102 from being urged outward away from covering the distal end of the needle 130 in the event an improper force is applied to one or both of the arms 101, 102 as illustrated in FIG. 29. FIG. 30 is an isometric view of the needle guard assembly 400 situated on the needle 130 in the first axial position. FIG. 31 is an isometric view of the needle guard assembly 400 situated on the needle 130 in the second axial position.

According to some implementations, the first portion 410 and elongate member 152 of needle guard 400 are unitarily constructed.

Like the implementation described above in conjunction with FIG. 24, it is appreciated that the needle guard 400 may be modified so that arm 102 terminates at a location just distal to formed portion 414. In such an implementation the formed portion 414 is continually urged into contact with the outer surface of the elongate member 152 with the distal section 107 of arm 101 situated to singularly cover the distal end 156 of the elongate member when the needle guard is situated in the second axial position on the needle 130.

It is important to note that many of the number of needle guard features disclosed herein (both above and below) are interchangeable among the numerous implementations disclosed and contemplated herein. For example, although some implementations disclose the use of features 113, 114 and other features 313, 314 and others 413, 414, it is appreciated that a combination of these features may be incorporated into a needle guard according to the inventions disclosed herein. Further, as an example, the variety of elongate members 152 and elongate features disclosed herein are interchangeable among the numerous implementations disclosed and contemplated herein.

Figure 32:
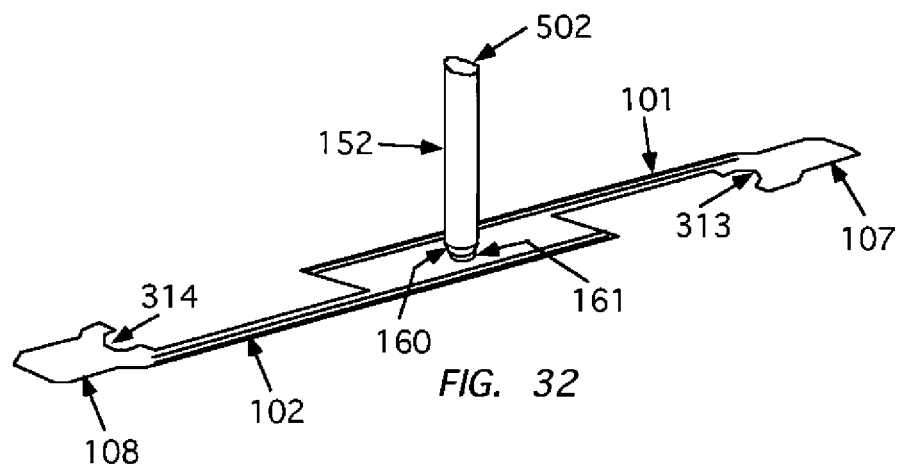
FIGS. 32 through 34 illustrate a needle guard assembly according to another implementation.
Figure 33:
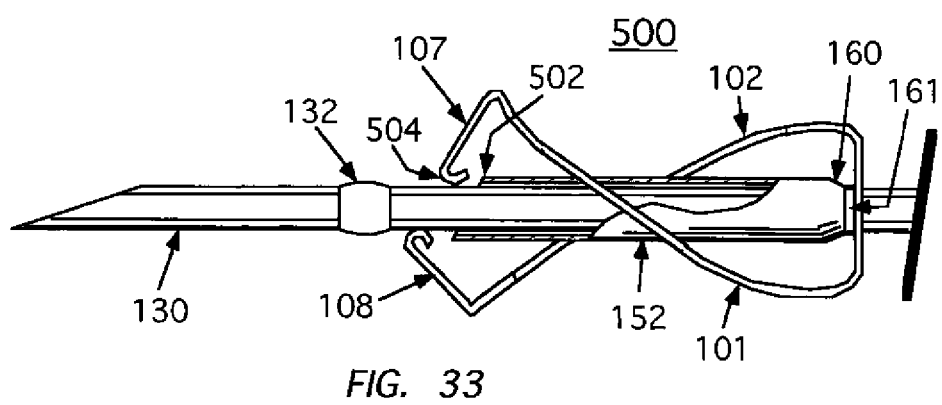
Figure 34:
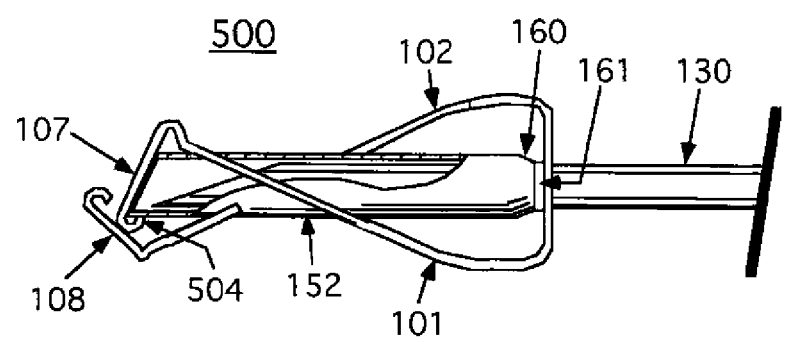

FIGS. 32 through 34 illustrate a needle guard assembly 500 similar to the needle guard assembly 300 described above except that the distal end 502 of the elongate member 152 comprises an oblique orientation with respect to the longitudinal axis of the elongate member and the distal section 107 of arm 101 is angularly oriented to assume the oblique orientation of the distal end 502 of the elongate member when the needle guard assembly 500 is in the second axial position as shown in FIG. 34. A proximal section of the elongate member 152 also includes a frusto-conical portion 160 and a reduced diameter portion 161 like that depicted in FIG. 15. Distal section 107 is preferably configured to exert a force on the distal end 502 of the elongate member 152 when the needle guard is in the second axial position. The lip 504 located at the distal end of section 107 is also oriented in a downward facing position and is situated to traverse the beveled distal opening of the elongate member 152 to provide a mechanical stop that inhibits the distal arm section 107 from separating from the distal end 502 of the elongate member when a compressive force or "pinch" is applied to one or both of arms 101 and 102.

According to some implementations the first portion and elongate member 152 of needle guard 500 are unitarily constructed.

A downward facing lip may be provided at the distal end of the distal sections 107 in the various implementations disclosed herein to inhibit the distal arm section 107 from separating from the distal end of the elongate member 152 when a compressive force or "pinch" is applied to one or both of arms 101 and 102. In some implementations the distal end of the elongate member 152 is provided with an indentation or kerf to interlock with a lip provided at a distal end of section 107.

Figure 35:
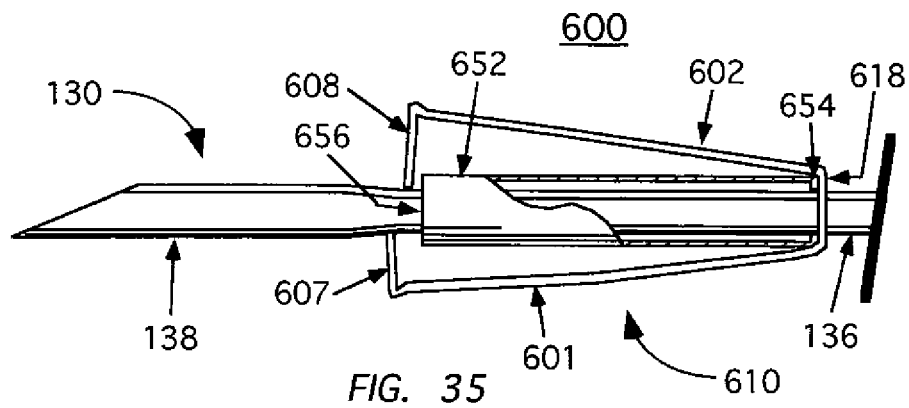
FIGS. 35 through 37 illustrate a needle guard assembly according to another implementation.
Figure 36:
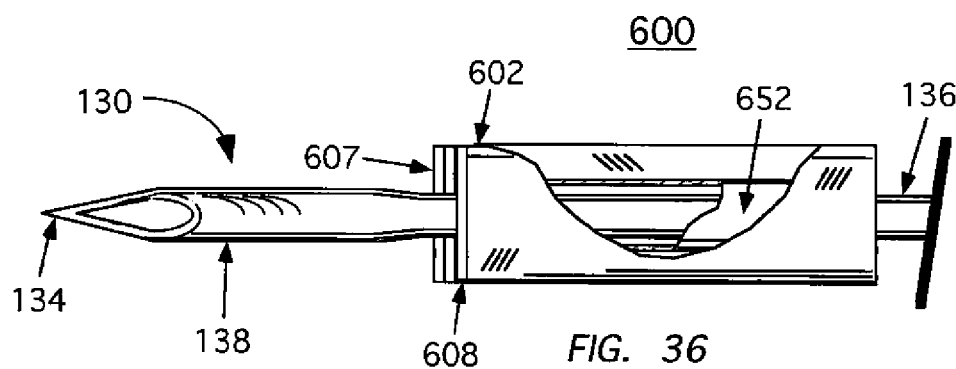
Figure 37:
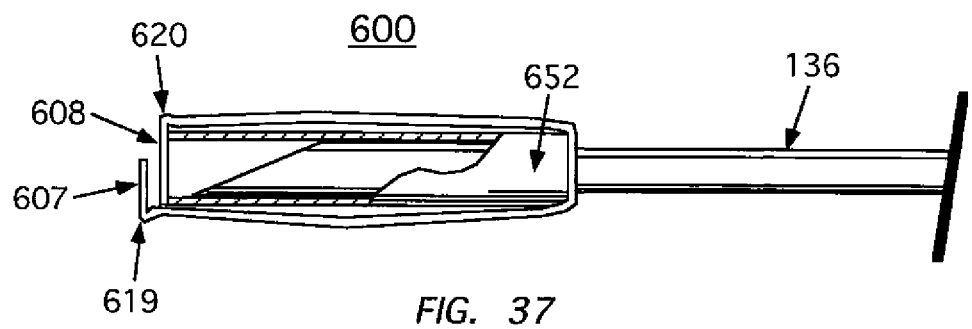

FIGS. 35 through 37 illustrate a needle guard 600 according to another implementation. The needle guard comprises a first portion 610 with an elongate member 652 integrated therein. In one implementation the first portion 610 includes first and second arms 601 and 602, respectively, that extend from opposite sides of a base 618. The first portion is preferably fabricated from a single piece of resilient material that is bent to form the base 618, arms 601, 602 and distal arm sections 607, 608. An aperture in the base 618 (not shown) is sized to receive a proximal portion 136 of the needle 130 and to guide the needle guard along the needle shaft as it transitions from a first axial position (as shown in FIGS. 35 and 36) to a second axial position to protect the distal end 134 of the needle (as shown in FIG. 37). The arms 601, 602 are hinged at the base 618 and are configured to assume an abutting relationship with the outer surface of the needle 130 when the needle guard 600 is situated in a first axial position with the distal end 134 of the needle is unprotected. An elongate member 652 having proximal and distal ends 654 and 656, respectively, is provided with an internal through passage 653 that extends between the two ends. The needle 130 comprises a proximal shaft portion 136 and a flared distal shaft portion 138 of increasing diameter. In use, the elongate member 652 is situated to reside in the first portion 610 between the base 618 and the distal arm section 608. In one implementation the aperture in base 618 is sized to engage with flared distal shaft portion 118 to stop the needle guard 600 in the second axial position as depicted in FIG. 37 with the entirety of the internal passage 653 of the elongate member 652 having a diameter sufficient to be advanced so that the distal end 656 of the elongate member extends to or past the distal tip of the needle. In another implementation the proximal end of the elongate member 652 is provided with a reduced internal diameter portion that acts to stop the needle guard in the second axial position. In another implementation a sleeve or bushing is situated at the proximal end 654 of the elongate member 652 and includes an internal bore with diameter sufficient to act as the second axial position stop.

As illustrated in FIG. 37, substantially coincident with the distal end 656 of the elongate member 652 situated to cover the entirety of the distal end 134 of the needle 130, arms 601 and 602 disengage from the needle shaft and are urged inward by stored energy to cover the distal end of the elongate member. According to one implementation, distal arm section 608 is hinged at location 620 to provide a downward/proximally acting force on the distal end 656 of elongate member 652. In one implementation arms 601 and 602 are provided with protrusions 619 and 620 that function to interact with one or more internal features of a catheter hub to releasably secure the needle guard 600 within the catheter hub in a manner similarly described with respect to FIG. 38.

According to some implementations the first portion and elongate member 652 of needle guard 600 are unitarily constructed.

As discussed above, FIG. 38 is a side view of a safety intravenous catheter assembly 700 in a ready to use operative position according to one implementation. Assembly 700 includes a needle 130 with a sharpened distal tip 134 with an internal lumen extending from a proximal end 140 to the tip 134. A change in profile 132 on the needle shaft functions to stop the needle guard 100 in the second axial position as previously described. A proximal end portion of the needle 130 is attached to a needle hub 704 having proximal protrusions 706 for attaching a male luer fitting. The proximal end 140 of the needle being situated in a flashback chamber 708 of the needle hub 704. As previously discussed, the needle guard 100 is releasable secured in the catheter hub 702 by the engagement of protrusions 117 and 116 with a feature or features 703 situated on the inner wall of the catheter hub. The proximal end of the catheter hub 702 is operatively engaged with the distal end of the needle hub 704. A tubular catheter 710 extends distally from the distal end of the catheter hub 702 in coaxial relationship with needle 130 and terminates proximal to the needle tip 134 so that the needle tip is exposed for puncturing a blood vessel and introducing the catheter 710. In use, upon the catheter 710 being properly introduced into the vessel of a patient, the needle hub 704 is pulled proximally to retract the needle tip 134 from the patient and into the needle tip guard 100. As the needle is withdrawn, the needle guard 100 is secured within the needle hub 702 by the outward force exerted by protrusions 117 and 116. The location of the change in profile 132 on the needle 130 in combination with the dimensional characteristics of the needle guard 100 result in the distal tip 134 being fully housed within the elongate member 152 substantially coincident with the change in profile 132 being stopped on the needle guard. Upon the distal tip 134 entering the distal end 156 of the elongate member 152, the distal arm segments 107 and 108 disengage the needle shaft and are urged inward to cover the distal end 156 of the elongate member by stored energy in the arms 101 and 102. At the same time protrusions 107 and 108 disengage with the catheter hub 702 to permit the needle guard 100 and needle 130 to be fully removed from the catheter hub 702. When the needle guard 100 is in the ready position the distal arm segment 107 of arm 101 is biased radially inward to rest on an outer surface 151 of the elongate member 152.

FIGS. 39 and 40 illustrate an intravenous catheter assembly 800 according to another implementation. Assembly 800 is similar to that of assembly 700 discussed above. A difference lies in the manner in which the needle guard 100 is releasably secured within the catheter hub 802. In the assembly 800, in lieu of the use of protrusion 117, 118 formed on arms 101, 102, resilient tabs 810 and 811 situated at or near the base of the needle guard 100 protrude outward to engage one or more features 803 of the inner wall of the catheter hub 802. The outer engaging surfaces of tabs 810 and 811 are preferably arcuate to coincide with the curvature of the inner wall of the catheter hub 802. The one or more features 803 may comprise a recess, undercut, void, groove, protruding feature, etc., configured either annularly or in segments about the inner wall. The resilient tabs 810 and 811 are configured to exert an outward force to cause the engaging surfaces to engage with the one or more features 803 when the assembly 800 is in the ready position or during the withdrawal of the needle 130 into the needle guard 100. The engagement force of tabs 810 and 811 is sufficiently low to permit the tabs to disengage from the one or more features 803 (see FIG. 40) when a proximal force is applied to the needle guard upon the change in profile 132 of the needle engaging needle guard stop.

FIG. 41 illustrates a needle guard assembly 900 situated in a protective position on a Huber needle, the Huber needle being characterized by a change in axis or bend near the distal end of the needle 190. The needle guard assembly 900 is in many respects similar to some of the implementations disclosed and described above except that the internal passage extending through the elongate member 952 is configured in such a way that permits the distal portion 958 of the elongate member to maneuver around the change in axis and to cant as the needle 190 is retracted into a protected position within the elongate member 952. In one implementation a proximal end section 960 of the elongate member 952 is provided with a reduced inner diameter segment of an appropriate length that stops the needle guard on the change in axis. In other implementations, a sleeve of sufficient length with a reduced inner diameter is attached to or otherwise coupled to the proximal end of elongate member 952. In other implementations a change in profile or enlargement is situated proximal to the change in axis to act as the stop.

Numerous exemplary implementations have been disclosed and described herein. It is to be appreciated however, that the present invention is in no way to be construed as to being limited to these examples

What is claimed is:
1. A needle assembly comprising:
a needle having a longitudinal axis and a distal end section comprising a distal tip;
an elongate member including an open distal end, a proximal end portion and a through passage having a longitudinal axis through which the needle passes; and
an axially extending arm that extends from a base, the base comprising an aperture, at least a portion of the needle and at least a portion of the proximal end portion of the elongate member residing in the aperture, the axially extending arm having a radially extending end segment, in a non-shielding position of the axially extending arm the radially extending end segment does not extend over the open distal end of the elongate member, in a shielding position of the axially extending arm at least a portion of the distal end section of the needle is positioned inside the elongate member and the radially extending end segment extends over the open distal end of the elongate member to impede distal movement of the needle.

2. The needle assembly according to claim 1, wherein the dimensional characteristics of the proximal end portion of the elongate member and of the aperture in the base cause the longitudinal axis of the needle to be substantially coaxially aligned with the longitudinal axis of the elongate member when the axially extending arm is in the non-shielding position.

3. The needle assembly according to claim 2, wherein the axially extending arm includes a proximal section, a mid-section and a distal section, the proximal section having a first width and the distal section having a second width, the mid-section having a portion of a reduced width, the reduced width being less than one or both of the first and second widths so that an indentation is provided in a side of the axially extending arm, the axially extending arm intersecting the elongate member along the reduced width portion of the mid-section of the axially extending arm located between the proximal and distal sections.

4. The needle assembly according to claim 3, wherein no part of the reduced width portion of the axially extending arm contacts the elongate member when the axially extending arm is in the non-shielding position.

5. The needle assembly according to claim 3, wherein the needle comprises a change in profile with an enlarged cross-sectional area and the elongate member includes a through passage through which the needle passes, the through passage having a reduced cross-sectional area that is smaller than the enlarged cross-sectional area of the change in profile, the through passage having a distal cross-sectional area that is larger than the enlarged cross-sectional area of the change in profile, the elongate member having a length such that substantially coincident with the change of profile engaging the proximal reduced cross-sectional area of the through passage the entirety of the distal tip of the needle is positioned to reside within the through passage of the elongate member.

6. The needle assembly according to claim 3, wherein no part of the radially extending end segment of the axially extending arm resides inside the through passage when the axially extending arm is in the shielding position.

7. The needle assembly according to claim 2, wherein the elongate member is cylindrical and an outer circumference of the proximal end portion of the elongate member has a reduced diameter in respect to the outer circumference of the remainder of the elongate member.

8. The needle assembly according to claim 1, wherein the elongate member is cylindrical and an outer circumference of the proximal end portion of the elongate member has a reduced diameter in respect to the outer circumference of the remainder of the elongate member.

9. The needle assembly according to claim 8, wherein the axially extending arm includes a proximal section, a mid-section and a distal section, the proximal section having a first width and the distal section having a second width, the mid-section having a portion of a reduced width, the reduced width being less than one or both of the first and second widths so that an indentation is provided in a side of the axially extending arm, the axially extending arm intersecting the elongate member along the reduced width portion of the mid-section of the axially extending arm located between the proximal and distal sections.

10. The needle assembly according to claim 9, wherein no part of the reduced width portion of the axially extending arm contacts the elongate member when the axially extending arm is in the non-shielding position.

11. The needle assembly according to claim 9, wherein the needle comprises a change in profile with an enlarged cross-sectional area and the elongate member includes a through passage through which the needle passes, the through passage having a reduced cross-sectional area that is smaller than the enlarged cross-sectional area of the change in profile, the through passage having a distal cross-sectional area that is larger than the enlarged cross-sectional area of the change in profile, the elongate member having a length such that substantially coincident with the change of profile engaging the proximal reduced cross-sectional area of the through passage the entirety of the distal tip of the needle is positioned to reside within the through passage of the elongate member.

12. The needle assembly according to claim 9, wherein no part of the radially extending end segment of the axially extending arm resides inside the through passage when the axially extending arm is in the shielding position.

13. The needle assembly according to claim 1, wherein the axially extending arm includes a proximal section, a mid-section and a distal section, the proximal section having a first width and the distal section having a second width, the mid-section having a portion of a reduced width, the reduced width being less than one or both of the first and second widths so that an indentation is provided in a side of the axially extending arm, the axially extending arm intersecting the elongate member along the reduced width portion of the mid-section of the axially extending arm located between the proximal and distal sections.

14. The needle assembly according to claim 13, wherein no part of the reduced width portion of the axially extending arm contacts the elongate member when the axially extending arm is in the non-shielding position.

15. The needle assembly according to claim 1, wherein the needle comprises a change in profile with an enlarged cross-sectional area and the elongate member includes a through passage through which the needle passes, the through passage having a reduced cross-sectional area that is smaller than the enlarged cross-sectional area of the change in profile, the through passage having a distal cross-sectional area that is larger than the enlarged cross-sectional area of the change in profile.

16. The needle assembly according to claim 15, wherein the elongate member has a length such that substantially coincident with the change of profile engaging the proximal reduced cross-sectional area of the through passage the entirety of the distal tip of the needle is positioned to reside within the through passage of the elongate member.

17. The needle assembly according to claim 1, wherein no part of the radially extending end segment of the axially extending arm resides inside the through passage when the axially extending arm is in the shielding position.

18. The needle assembly according to claim 1, wherein the base and the axially extending arm are constructed of a single piece of material.

19. The needle assembly according to claim 1, wherein when the axially extending arm is in the shielding position the elongate member completely surrounds the distal end section of the needle.

20. The needle assembly according to claim 1, further comprising a catheter hub wherein which the axially extending arm resides when the radially extending end segment is in the non-shielding position, the axially extending arm including a protrusion that engages with one or more features located in an interior of the catheter hub to releasably secure the axially extending arm in the catheter hub.

* * * * *